(12) United States Patent
Singer et al.

(10) Patent No.: US 8,114,855 B2
(45) Date of Patent: Feb. 14, 2012

(54) LOW DENSITY COSMETIC FORMULATIONS, COSMETIC PRODUCTS CONTAINING THE SAME AND METHODS OF TREATING HAIR, NAILS AND/OR SKIN USING THE SAME

(75) Inventors: Jim M. Singer, South Orange, NJ (US); Jolene A. Morris, North Plainfield, NJ (US)

(73) Assignee: L'Oreal, Paris (FR)

( * ) Notice: Subject to any disclaimer, the term of this patent is extended or adjusted under 35 U.S.C. 154(b) by 647 days.

(21) Appl. No.: 11/943,719

(22) Filed: Nov. 21, 2007

(65) Prior Publication Data

US 2008/0119413 A1 May 22, 2008

Related U.S. Application Data

(60) Provisional application No. 60/860,582, filed on Nov. 22, 2006.

(51) Int. Cl.
*A61K 31/715* (2006.01)
*A61K 47/00* (2006.01)
*A61K 8/02* (2006.01)

(52) U.S. Cl. ........ 514/54; 514/53; 514/57; 514/60; 514/844; 514/846; 514/880; 514/944; 424/401

(58) Field of Classification Search ............ 514/53, 514/54, 57, 60, 844, 846, 880, 944; 424/401
See application file for complete search history.

(56) References Cited

U.S. PATENT DOCUMENTS

| | | | |
|---|---|---|---|
| 6,045,779 A * | 4/2000 | Mueller et al. ............ 424/47 |
| 6,063,368 A | 5/2000 | Kapsner et al. | |
| 6,413,505 B1 | 7/2002 | Vitale et al. | |
| 6,562,325 B2 | 5/2003 | Vitale et al. | |
| 6,627,183 B1 | 9/2003 | Young et al. | |
| 7,488,709 B2 * | 2/2009 | Ribery et al. ............ 510/276 |
| 2001/0022967 A1 | 9/2001 | Brandt et al. | |
| 2004/0076651 A1 | 4/2004 | Brocks et al. | |
| 2004/0131576 A1 | 7/2004 | Decoster et al. | |
| 2004/0234486 A1 | 11/2004 | Hashimoto | |
| 2004/0265243 A1 | 12/2004 | Albrecht et al. | |
| 2005/0032656 A1 | 2/2005 | Strassner et al. | |

FOREIGN PATENT DOCUMENTS

| | | |
|---|---|---|
| DE | 4327699 A1 | 2/1995 |
| EP | 0925775 A2 | 6/1999 |
| EP | 1092417 A1 | 4/2001 |
| EP | 1092418 A1 | 4/2001 |
| EP | 1374838 A1 | 1/2004 |
| FR | 2850017 A1 | 7/2004 |
| WO | WO-2004073665 A1 | 9/2004 |

OTHER PUBLICATIONS

European Search Report in Application No. 07254555 dated Mar. 13, 2009.

* cited by examiner

*Primary Examiner* — Shaojia Anna Jiang
*Assistant Examiner* — Everett White
(74) *Attorney, Agent, or Firm* — Connolly Bove Lodge & Hutz LLP

(57) ABSTRACT

Low density cosmetic formulations which comprise: (a) a cosmetic mixture; and (b) a gas incorporated in the cosmetic mixture; wherein the cosmetic mixture comprises (i) an alk(en)ylpolyglycoside, (ii) a quaternary ammonium polymer, and (iii) a thickener, are described along with suitable cosmetic mixtures for forming such low density formulations, methods of forming such formulations and methods of treating skin, hair, nails and/or combinations thereof by contacting the skin, hair and/or nails with such formulations and/or products containing such formulations.

24 Claims, No Drawings

LOW DENSITY COSMETIC FORMULATIONS, COSMETIC PRODUCTS CONTAINING THE SAME AND METHODS OF TREATING HAIR, NAILS AND/OR SKIN USING THE SAME

RELATED APPLICATIONS

This application claims priority to U.S. Provisional Application No. 60/860,582 filed Nov. 22, 2006, disclosure of which is incorporated herein by reference.

BACKGROUND OF THE INVENTION

Many consumers of cosmetic products show an increasing desire for new products which are pleasing to the senses both on application and in use and which have new, interesting and/or pleasing textures, preferably without any sacrifice of functional performance. Most existing cosmetic compositions are generally provided in forms such as solutions, pastes, aerosols, foams, gels and creams which are alternatively either essentially fluid or heavy and thick.

Conventional cosmetic compositions in the form of creams are generally emulsions. Emulsions comprise an aqueous phase and an oily phase dispersed in one another either as an oil-in-water (O/W) emulsion where the external phase is the aqueous phase, or as water-in-oil (W/O) emulsions comprising an oily external phase. While such emulsions are commonplace in cosmetic formulations and can provide various positive effects such as moisturizing, they can feel heavy on the skin and hair and often impart an oily feel upon application.

Other conventional cosmetic compositions delivered in the form of a foam can alleviate the heavy feel associated with creamy emulsion, but foams are generally not stable long term and will eventually collapse on standing or in storage. Other conventional cosmetic compositions forms have drawbacks as well. For example, aerosols generally contain flammable contents under pressure which creates some danger and upon use they expel propellant gases into the atmosphere. While cosmetic compositions in the form of solutions and fluid creams can address some of these concerns, such formulations are not always suitable for various applications where a liquid or low viscosity form is not convenient such as, for example, controlled spot application to the skin or application to the hair outside of the shower or bath.

Attempts have been made to confer a novel texture on conventional emulsions by introducing air into the emulsions to give them a lighter texture and the appearance of a foam. However, such attempts at aerated emulsions suffered from the disadvantage of being relatively unstable, collapsing back to a thick emulsion or undergoing phase separation after a certain storage time. Various additives and combinations of certain polymers have been proposed for providing stable low density emulsions for cosmetic use but have failed to yield satisfactory formulations from both a sensory and functional perspective.

Thus, the provision of cosmetic products in the form of low density formulations, with or without the presence of an oil phase-containing emulsion, is desirable.

BRIEF SUMMARY OF THE INVENTION

The present invention is directed to cosmetic compositions, in general, and more particularly to low density cosmetic formulations comprising a cosmetic mixture in accordance with one aspect of the present invention and a gas incorporated in the cosmetic mixture. The low density cosmetic formulations of the present invention are preferably in the form of gels or creams, but are not limited to such forms and may not fit neatly into classically defined physical forms as the present invention includes thickened cosmetic products that exhibit novel textural aesthetics.

The present invention is also directed, in general, to methods of forming such low density cosmetic formulations and methods of treating hair, nails and/or skin by contacting the substrate, (skin, hair, nails, lips, etc.), with an inventive low density cosmetic formulation. The present invention also includes cosmetic mixtures which can be used to prepare low density cosmetic formulations according to one or more embodiments of the invention.

Various embodiments of the present invention are directed to low density cosmetic formulations comprising a cosmetic mixture and a gas incorporated in the cosmetic mixture, wherein the mixture comprises an alk(en)polyglycoside, a quaternary ammonium polymer and a thickener. As used herein, "low density" refers to a product having a density less than about 1 at approximately 25° C. (~room temperature) and standard atmospheric pressure (~1 atm).

Another embodiment of the present invention is directed to low density cosmetic formulations which comprise: (a) cosmetic mixture; and (b) air incorporated in the cosmetic mixture; wherein the cosmetic mixture comprises a decylglucoside, a quaternized cellulosic polymer, a guar gum and a hydroxyethylcellulose, wherein the decylglucoside is present in an amount of 0.5 to 5% by weight, the quaternary ammonium polymer is present in an amount of 0.1 to 2% by weight, the guar gum is present in an amount of 0.5 to 3% by weight and the hydroxyethylcellulose is present in an amount of 0.5 to 2.0% by weight, all weights being based on the cosmetic mixture.

Another embodiment of the present invention is directed to cosmetic mixtures comprising an alk(en)polyglycoside, a quaternary ammonium polymer and a thickener which can be used to prepare low density cosmetic formulations according to various other embodiments of the invention. Certain preferred embodiments are directed to cosmetic mixtures comprising a decylglucoside, a quaternized cellulosic polymer, a guar gum and a hydroxyethylcellulose, which compositions can preferably be used to prepare certain embodiments of the inventive low density cosmetic formulations.

Various other embodiments of the present invention are directed to methods of forming stable low density cosmetic formulations, which comprise providing a cosmetic mixture in accordance with an embodiment of the present invention and incorporating a gas into the mixture.

Other embodiments of the present invention are directed to methods of treating hair, nails and/or skin comprising providing a hair, nail and/or skin substrate to be treated, and contacting the substrate with a stable low density cosmetic formulation comprising: (a) a cosmetic mixture; and (b) a gas incorporated in the cosmetic mixture; wherein the cosmetic mixture comprises (i) an alk(en)ylpolyglycoside, (ii) a quaternary ammonium polymer, and (iii) a thickener.

Various treatment methods included in the methods of the present invention are, for example, styling hair, fortifying hair, moisturizing hair, cleaning hair, coloring/dyeing hair, lightening and/or highlighting hair, perming hair, relaxing hair, post treatments after chemically treating hair or skin, conditioning hair, treating the scalp, protecting (e.g., from UV radiation) skin or hair, protecting and treating nails and lips, cleaning skin, moisturizing skin, making up skin and hair (e.g., with color cosmetics such as foundations, lipsticks, eyeshadows, blushes and/or mascaras) and delivering nutrients, vitamins and/or beneficial active cosmetic ingredients to the skin.

DETAILED DESCRIPTION OF THE INVENTION

Cosmetic mixtures in accordance with the various embodiments of the present invention can provide low density cosmetic formulations when a gas is incorporated therein. The low density cosmetic formulations in accordance with the present invention provide a thick and malleable cosmetic product which is generally pleasing to the senses, particularly feel, upon application and is not heavy. Moreover, the low density cosmetic formulations in accordance with the various embodiments of the present invention are stable over long periods of time and do not collapse allowing the incorporated gas to escape. Generally, the low density cosmetic formulations of the present invention exist stably at room temperature and upon storage for at least two or more weeks, more preferably a month or more, even more preferably two months or more and most preferably for at least a year. As used herein, "stability" and/or "stable" refer to cosmetic formulations in which there is little or no pH change over time and the formulation does not collapse significantly (i.e., a decrease in volume of more than 10%) as measured in a graduated container. Formulations can be evaluated for stability at room temperature and/or alternate temperatures (e.g., 6° C., 37° C., and 45° C.) in varying increments of time from 1 week to 52 weeks by measuring pH initially and at incremental times as well as by evaluating the physical appearance of the formulation in a graduated container.

Cosmetic mixtures in accordance with various embodiments of the present invention (and thus, low density cosmetic formulations prepared using the same) can include one or more alk(en)ylpolyglycosides. Alk(en)ylpolyglycosides suitable for use in accordance with cosmetic mixtures according to embodiments of the present invention generally correspond to formula I:

$$R\text{—}O[G]_x \qquad (I)$$

wherein R represents a linear or branched, saturated or unsaturated hydrocarbon moiety having from 6 to 22 carbon atoms, G represents a sugar moiety and x is a number from 1 to 10. Preferably, R represents a hydrocarbon moiety having from 6 to 16 carbon atoms. More preferably, R represents a hydrocarbon moiety having from 8 to 14 carbon atoms. Most preferably, R represents a $C_{10}$ hydrocarbon moiety.

In certain embodiments, the alk(en)ylpolyglycoside component can comprise mixtures of two or more alk(en)ylpolyglycosides with different R groups, different sugar moieties, and/or different values for x (i.e., degree of polymerization, or DP). In certain embodiments, the alk(en)ylpolyglycoside component can comprise a mixture of two or more alk(en)ylpolyglycosides having hydrocarbon moieties selected from $C_6$, $C_8$, $C_{10}$, $C_{12}$, $C_{14}$ and $C_{16}$ hydrocarbons. Preferred alk(en)ylpolyglycoside components comprised of a mixture of two or more alk(en)ylpolyglycosides include at least some alk(en)ylpolyglycoside having a $C_{10}$ hydrocarbon moiety.

A particularly preferred alk(en)ylpolyglycoside component suitable for use in cosmetic mixtures according to the various embodiments of the invention and the low density cosmetic formulations prepared from such mixtures is PLANTACARE™ 2000UP, which is commercially available from Cognis Corporation (Ambler, Pa.).

Suitable sugar moieties represented in formula (I) by G include pentoses and hexoses. Preferably, the sugar moiety (or moieties where x is greater than 1) can include hexoses such as glucose. In formula (I), x represents a number of from 1 to 10 and preferably from 1 to 4, more preferably 1 to 3. The sugar moieties may be the same or different and are preferably all glucose moieties. In certain preferred embodiments of the present invention, the alk(en)ylpolyglycoside component comprises decylglucosides with an average degree of polymerization of about 1.2 to 1.4.

Cosmetic mixtures (and formulations prepared using such mixtures) in accordance with various embodiments of the present invention include a quaternary ammonium polymer. Quaternary ammonium polymers suitable for use in accordance with the various embodiments of the present preferably include quaternized cellulosic polymers. More preferably, the quaternary ammonium polymer present in the cosmetic mixtures of the various embodiments of the invention includes a quaternized derivative of a hydroxyalkylcellulose. A particularly preferred quaternary ammonium polymer suitable for use in the cosmetic mixtures of the present invention is a polyquaternium-10. Polyquaternium-10 refers generally to a salt of a hydroxyethylcellulose reacted with trimethyl ammonium substituted epoxide.

Cosmetic mixtures in accordance with the present invention may include two or more quaternary ammonium polymers. In certain preferred embodiments of the present invention, the cosmetic mixture comprises a quaternized derivative of a hydroxyalkylcellulose and one or more additional quaternary ammonium polymers. In certain more preferred embodiments of the present invention, the cosmetic mixture comprises a polyquaternium-10 and one or more additional quaternary ammonium polymers. One preferred embodiment of a cosmetic mixture according to the invention comprises a polyquaternium-4, a polyquaternium-10 and a polyquaternium-11.

Cosmetic mixtures (and formulations prepared using such mixtures) in accordance with various embodiments of the present invention also include a thickener. Suitable thickeners can include synthetic polymers such as, for example, polyvinylpyrrolidone or the cross-linked polyacrylates (e.g., Carbomers, Carbopols), polymers of natural origin, particularly polysaccharides and derivatives thereof, for example gums, starches, gelatins, celluloses and derivatives thereof such as carboxymethylcellulose, hydroxypropylcellulose, methylcellulose, hydroxypropylmethylcellulose or hydroxyethylcellulose, microcrystalline cellulose and extracts of algae such as agar, carrageenan or the alginates, as well as carouba gum, guar gum and the derivatives thereof, for example, alkylated or hydroxyalkylated guar, karaya gum, xanthan gum, gum arabic, and pectins, and inorganic thickeners such as the hectorites, bentonites, aluminum silicates and magnesium silicates, or a mixture of said substances.

Preferably, a thickener in accordance with various embodiments of the present invention will include a guar gum and/or a cellulose. Particularly preferred celluloses include hydroxyethylcelluloses. In certain preferred embodiments of the present invention, the cosmetic mixtures comprise a guar gum and a hydroxyethyl cellulose mixture.

One preferred embodiment of cosmetic mixtures according to the present invention includes mixtures which comprise a decylglucoside, most preferably PLANTAREN® 2000UP, a polyquaternium-10, guar gum and hydroxyethylcellulose.

The alk(en)ylpolyglycoside component may be present in the cosmetic mixtures in accordance with various embodiments of the present invention in an amount of 0.1 to 25% by weight. Preferably, the alk(en)ylpolyglycoside component is present in the cosmetic mixtures of the present invention in an amount of 0.2 to 15% by weight, and most preferably in an amount of 0.5 to 5% by weight.

The quaternary ammonium polymer component may be present in the cosmetic mixtures in accordance with various embodiments of the present invention in an amount of 0.1 to 10% by weight. Preferably, the quaternary ammonium polymer component is present in the cosmetic mixtures of the present invention in an amount of 0.1 to 10% by weight, and most preferably in an amount of 0.5 to 5% by weight.

The thickener component may be present in the cosmetic mixtures in accordance with various embodiments of the present invention in an amount of 0.1 to 10% by weight. Preferably, the thickener component is present in the cosmetic mixtures of the present invention in an amount of 0.5 to 5% by weight, and most preferably in an amount of 0.5 to 3% by weight.

Low density cosmetic formulations in accordance with the various embodiments of the present invention include a gas incorporated in a cosmetic mixture in accordance with any of the embodiments of the inventive compositions described above. Suitable gases which can be incorporated in the cosmetic mixtures described herein to provide a low density cosmetic formulation in accordance with the present invention include, but are not limited to, air, inert gases, carbon dioxide and mixtures thereof. Preferred inert gases include nitrogen, helium, and argon. In certain preferred embodiments of the present invention, the gas incorporated in the mixture comprises air. Any of the suitable gases can be compressed when introduced into the mixture.

A gas is incorporated in the cosmetic mixture in such an amount to provide a low density cosmetic formulation. Thus, gas is incorporated in an amount necessary to form a product (e.g., cream, gel, etc.) having a density less than about 1 g/mL when measured at about room temperature and standard atmospheric pressure. Preferably, the gas is incorporated in an amount necessary to form a product having a density less than about 0.9 g/mL. More preferably, the gas is incorporated in an amount necessary to form a product having a density of about 0.2 to about 0.8 g/mL. Most preferably, the gas is incorporated in an amount necessary to form a product having a density of about 0.5 to about 0.8 g/mL. The amount of gas necessary to obtain the desired density can be as much as 30% by volume, and it may range, for example, from 40 to 80% by volume. The exact amount of gas necessary to achieve a particular density product may vary slightly depending upon the gas or mixture of gases used.

Cosmetic mixtures according to the present invention can further comprise an oil and may also contain an oil phase to provide an emulsion for use in preparing low density cosmetic formulations. The nature of the oil component or oil phase of an emulsion (hereinafter collectively referred to as "the oil phase" regardless of whether the oil component is emulsified in the mixture or not) in accordance with such embodiments of the invention is not critical. The oil phase can be composed of any fatty substance conventionally used in the cosmetic and dermatological fields, and preferably an oil rather than a fat or a wax. The oil phase can contain one or more oils, preferably at least 1% by weight of at least one oil and better at least 2% by weight of at least one oil, with respect to the total weight of the composition.

Suitable oils include, but are not limited to, vegetable oils, such as apricot oil, mineral oils, such as liquid petrolatum, synthetic oils, such as isohexadecane; volatile or non-volatile silicon oils; and fluorinated oils.

In embodiments of the present invention where the cosmetic mixture comprises an emulsion, the oil phase may advantageously be present in the emulsion in an amount of 1 to 40% by weight, preferably from 2 to 30% and better still from 5 to 20% by weight, based the weight of the emulsion.

In embodiments of the present invention where the cosmetic mixture comprises an emulsion, the mixture may further include an emulsifier. Any suitable emulsifier known in the art or to be developed which is compatible with the other components of the mixture and cosmetically acceptable can be used. The emulsions according to the invention can comprise, for example, from 0.5 to 30%, preferably from 2 to 15% and better still from 4 to 10% by weight of emulsifier(s) based on the total weight of the emulsion.

Cosmetic mixtures according to the present invention and low density cosmetic formulations prepared by incorporating a gas in a cosmetic mixture may contain a variety of additional ingredients. For example, the compositions of the invention can also comprise adjuvants usual in the cosmetics field, such as active principles, botanical and/or vegetable and/or fruit extracts, humectants, preservatives, antioxidants, complexing agents, solvents, fragrances, UV screening agents, bactericides, odor absorbers, coloring materials (pigments or soluble dyes) and lipid vesicles. The compositions of the invention can also comprise acrylates, silicones and other polymeric ingredients (e.g., resins, film formers, elastomers, etc.). The amounts of these various additional ingredients are generally those conventionally used in the field of cosmetics, for example from 0.01 to 20% of the total weight of the mixture.

Low density cosmetic formulations according to the present invention can be formed by incorporating a gas into a cosmetic mixture according to any embodiment described herein. The gas may be incorporated in any suitable manner including, but not limited to simple mixing in contact with an atmosphere containing a suitable gas or even ambient conditions, aeration or other methods of injecting a gas into or through the mixture and by use of gas expansion devices known in the art or which are to be developed.

In several preferred embodiments of the present invention, the introduction of the gas, preferably air, into the cosmetic mixture is carried out in an expansion device comprising a mixing head having a rotor and a stator, such as, for example, the "Minimondo-type Mondomixer" commercially available from Mondomix. The mixture is transported via a pump into the expansion head, where the mixture and the gas are simultaneously injected and homogeneously mixed by virtue of the cutting action of the lugs of the rotor and stator of the device, which provide even distribution of the gas in the mixture. The speed of the rotor of the device, the temperature of the vessel, gas pressure and flowrate of the gas are appropriately regulated. The pressure of the mixing head is regulated by a pressure regulator. The flow rate of the low density cosmetic formulation at the outlet of the device depends on the rate of the pump at the vessel outlet.

Preferably, in the expansion device, the stirring speed during the introduction of the gas is approximately 100 to 1000 revolutions/minute and more preferably, approximately 800 revolutions/minute. The temperature of the vessel is approximately room temperature (e.g., about 25 to 30° C.), although heating can be carried out if desired. The gas pressure is approximately 2-5 bar, and preferably about 3 bar. Backpressure can be about 1.5 bar. Bulk flowrate of the mixture can be about 20-25 kg/hour. The gas bubbles in the low density cosmetic formulation obtained according to the embodiments of the invention using a gas expansion device can generally have a size ranging from about 20 µm to about 6000 µm, preferably from about 100 µm to about 3000 µm. In general, it is advantageous from an aesthetic perspective that at least a portion of the bubbles are visible without magnification.

Methods in accordance with other embodiments of the invention include treating hair, nails and/or skin with a low density cosmetic formulation according to one or more embodiments of that aspect of the present invention. Such methods generally include providing a hair or skin substrate to be treated, preferably hair, and contacting the substrate with a low density cosmetic formulation according to an embodiment of the invention. Methods in accordance with this aspect of the invention can include application of the cosmetic formulation to the substrate with any of direct application to the dry substrate, wetting, lathering, rinsing, allowing to stand followed by rinsing, blow-drying, dyeing, lightening, highlighting, perming, relaxing, making up skin, nails, lips and/or hair, moisturizing and massaging. Any of these additional steps or combinations thereof can be carried out prior to, simultaneously with or subsequent to the application of the low density cosmetic formulation.

The invention will now be described in further detail with reference to the following non-limiting examples.

EXAMPLES

Mixture Example I

A cosmetic composition in accordance with one embodiment of the invention was prepared by combining and mixing the following ingredients listed in Table 1. The composition was subsequently used to prepare a low density cosmetic formulation in accordance with another embodiment of the invention by incorporating air into the composition. The components listed in Table 1 were mixed in the amounts indicated in the second column of the table wherein all amounts are expressed in percentage by weight based on the total weight of the composition.

TABLE 1

| INCI Name | |
| --- | --- |
| Stearic Acid | 0.95 |
| Laureth-23 | 1.2 |
| Cetearyl Alcohol | 2 |
| Glyceryl Stearate | 1 |
| PEG-100 Stearate | 1 |
| Decyl Glucoside | 1.6 |
| Polyquaternium-10 | 0.73 |
| Hydroxypropyl Guar | 2.5 |
| Hydroxyethylcellulose | 1 |
| Potato Starch Modified | 0.43 |
| Polyquaternium-4 | 0.5 |
| Polyquaternium-11 | 0.4 |
| Fragrance | 0.3 |
| Preservatives, adjuvants, UV filter | 1.88 |
| Q.S. water | |

Mixture Example II

A second cosmetic composition in accordance with one embodiment of the invention was prepared by combining and mixing the following ingredients listed in Table 2. The composition was subsequently used to prepare a low density cosmetic formulation in accordance with another embodiment of the invention by incorporating air into the composition. The components listed in Table 2 were mixed in the amounts indicated in the second column of the table wherein all amounts are expressed in percentage by weight based on the total weight of the composition.

TABLE 2

| INCI Name | |
| --- | --- |
| Stearic Acid | 0.95 |
| Laureth-23 | 1.2 |
| Cetearyl Alcohol | 2 |
| Glyceryl Stearate | 1 |
| PEG-100 Stearate | 1 |
| Decyl Glucoside | 1.6 |
| Polyquaternium-10 | 0.73 |
| Hydroxypropyl Guar | 2.5 |
| Hydroxyethylcellulose | 1 |
| Potato Starch Modified | 0.086 |
| Polyquaternium-4 | 0.4 |
| Polyquaternium-11 | 0.4 |
| Fragrance | 0.3 |
| Preservatives, adjuvants, UV filter | 1.88 |
| Q.S. water | |

Preparation Example I

The cosmetic mixture prepared in Mixture Example I was transferred to a Minimodo-type expansion device and fed to the pump of the expansion device. The mixture was then transported from the pump to the expansion head, into which it was injected with air and homogeneously mixed with the air. The flowrate of the mixture was approximately 23 kg/hour. The speed of the rotor was 800 revolutions/minute, the temperature of the vessel and pipes were approximately 25-30° C. and the air pressure was about 3 bar. Back pressure was about 1.5 bar.

Preparation Example II

The cosmetic mixture prepared in Mixture Example II was mixed in contact with ambient atmospheric air to provide a low density cosmetic formulation in accordance with one embodiment of the present invention.

In each of Preparation Examples I and II, a thick, malleable cosmetic formulation having a low density and a very light texture was obtained.

Comparative Example Thickening Lotion:

A thickening lotion lacking a cosmetic composition according to the invention was prepared for subsequent comparison versus the low density cosmetic formulations of the present invention with respect to salon performance regarding volume, texture, hair shapeability and other standard performance characterisitics. The conventional thickening lotion which is essentially fluid in comparison to the low density cosmetic formulations of the present invention was prepared by mixing the ingredients set forth below in Table 3. The ingredients were combined in the amounts listed in the second column wherein the numbers represent percentages by weight based on the total weight of the composition.

TABLE 3

| INCI Name | |
| --- | --- |
| Hydrolyzed Wheat Starch | 0.00275 |
| Magnesium Sulfate Magnesium Sulfate | 0.1 |
| Triethanolamine | 1.2 |
| Taurine | 0.1 |
| Disodium EDTA | 0.099 |
| VP/VA Copolymer | 2 |
| Alcohol Denat. | 0.725 |
| Peg/Ppg-17/18 Dimethicone | 1 |
| Sodium Polystyrene Sulfonate | 2.375 |
| Hydroxyethylcellulose | 1 |
| Carbomer | 1 |

TABLE 3-continued

| INCI Name | |
|---|---|
| Fragrance | 0.2 |
| Preservatives, adjuvants, UV filter | 4.976 |
| Q.S. water | |

Comparison I:

A low density cosmetic formulation according to Preparation Example I but without the fragrance, UV filter and various adjuvants was compared qualitatively against the comparative Thickening Lotion on three test subjects each for hair volumizing and shaping performance. The low density cosmetic formulation according to one embodiment of the invention outperformed the comparative Thickening Lotion in volumizing, thickening, combability, shapeability, stylability, hold and texture.

Performance Evaluation:

The low density cosmetic formulations of Preparation Examples I and II were each evaluated in hair styling applications on 12 to 13 test subjects each. On average, the low density cosmetic formulations prepared as described above in Preparation Examples I and II, performed similarly based on their volumizing, texture, hold, shapability and wet properties. The low density cosmetic formulations prepared as described above in Preparation Examples I and II performed as well or better than most conventional volumizing formulas, without leaving an oily residue or feeling heavy on the hair when dried.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

What is claimed is:

1. A cosmetic formulation in the form of a gel or cream having a density of less than 1 g/mL at 25° C. and standard atmospheric pressure (1 atm) comprising:
   (a) a cosmetic mixture; and
   (b) at least 30% by volume of a gas incorporated in the cosmetic mixture;
   wherein the cosmetic mixture comprises:
   (i) 0.1 to 25% by weight of at least one alk(en)ylpolyglycoside of general formula I:

$$R\text{---}O[G]_x \quad (I)$$

wherein R represents a saturated or unsaturated, linear or branched hydrocarbon moiety having from 6 to 22 carbon atoms, G represents a sugar moiety and x represents a number from 1 to 10,
   (ii) 0.01 to 10% by weight of at least one quaternary ammonium cellulosic polymer, and
   (iii) 0.01 to 10% by weight of at least one-thickener selected from the group consisting of a guar gum, a cellulose, and a cellulose derivative;
   wherein the percent weights are based on the total weight of the cosmetic mixture;
   wherein the cosmetic formulation does not decrease in volume at room temperature more than 10% for at least two weeks.

2. The cosmetic formulation according to claim 1, wherein the cosmetic mixture further comprises an oil component.

3. The cosmetic formulation according to claim 2, wherein the cosmetic mixture is an emulsion.

4. The cosmetic formulation according to claim 1, wherein the cosmetic formulation has a density equal to or less than 0.9 g/mL.

5. The cosmetic formulation according to claim 1, wherein the cosmetic formulation has a density of 0.2 to 0.8 g/mL.

6. The cosmetic formulation according to claim 1, wherein the cosmetic formulation has a density of 0.5 to 0.8 g/mL.

7. The cosmetic formulation according to claim 1, wherein R represents a saturated or unsaturated, linear or branched hydrocarbon moiety having from 8 to 16 carbon atoms, G represents a glucose moiety and x represents a number from 1 to 1.4.

8. The cosmetic formulation according to claim 1, wherein the at least one alk(en)ylpolyglycoside is decylglucoside.

9. The cosmetic formulation according to claim 1, wherein the at least one quaternized cellulosic polymer is polyquaternium-10.

10. The cosmetic formulation according to claim 1, wherein the gas is air.

11. The cosmetic formulation according to claim 1, wherein the gas is an inert gas.

12. The cosmetic formulation according to claim 1, wherein the gas is compressed.

13. The cosmetic formulation according to claim 1, wherein the gas comprises compressed air.

14. The cosmetic formulation according to claim 1, wherein the at least one alk(en)ylpolyglycoside is decylglucoside and the at least one thickener comprises a guar gum and a hydroxyethylcellulose.

15. A method of forming the cosmetic formulation of claim 1 comprising:
   (a) providing a cosmetic mixture comprising:
      (i) at least one alk(en)ylpolyglycoside,
      (ii) at least one quaternary ammonium cellulosic polymer, and
      (iii) at least a guar gum, a cellulose, a cellulose derivative, or a mixture thereof as a thickener; and
   (b) incorporating at least 30% by volume of a gas into the cosmetic mixture.

16. The method according to claim 15, wherein incorporating the gas comprises feeding the cosmetic mixture into an expansion device, and injecting air into the mixture.

17. The method of claim 16, wherein the mixture is not homogenized before being introduced into the expansion device.

18. A cosmetic formulation in the form of a gel or cream having a density of less than 1 g/mL at 25° C. and standard atmospheric pressure (1 atm) comprising:
   (a) cosmetic mixture; and
   (b) at least 30% by volume of air incorporated in the cosmetic mixture;
   wherein the cosmetic mixture comprises:
   (a) 0.5 to 5% by weight of a decylglucoside,
   (b) 0.1 to 2% by weight of a quaternized cellulosic polymer, and
   (c) a thickener comprising 0.5 to 3% by weight of a guar gum and 0.5 to 2% by weight of a hydroxyethylcellulose,
   wherein all weight percents are based on the total weight of the cosmetic mixture.

19. The cosmetic formulation according to claim 18, wherein the quaternized cellulosic polymer is polyquaternium-10.

20. A cosmetic formulation in the form of a gel or cream having a density of less than 1 g/mL at 25° C. and standard atmospheric pressure (1 atm) comprising:
   (a) a cosmetic mixture; and (b) at least 30% by volume of a gas incorporated in the cosmetic mixture; wherein the cosmetic mixture comprises:
 (i) 0.1 to 25% by weight of an alk(en)ylpolyglycoside,
 (ii) 0.1 to 10% by weight of a quaternary ammonium cellulosic polymer, and
 (iii) 0.1 to 10% of a thickener selected from the group consisting of a guar gum, a cellulose, and a cellulose derivative;
wherein all weight percents are based on the total weight of the cosmetic mixture; and
wherein the cosmetic formulation does not decrease in volume at room temperature more than 10% for at least two weeks.

21. The cosmetic formulation of claim 20, wherein the cosmetic formulation comprises from 40 to 80% by volume of a gas incorporated into the cosmetic mixture.

22. A method for treating a keratinous substrate comprising:
 providing a substrate to be treated selected from the group consisting of skin, nails, hair and combinations thereof; and
 contacting the substrate with a composition of claim 1.

23. The method according to claim 22, wherein the substrate comprises hair.

24. The method according to claim 22, wherein the substrate comprises skin.

* * * * *